United States Patent [19]

Möller et al.

[11] 4,081,596
[45] Mar. 28, 1978

[54] PYRAZOL-5-ONES

[75] Inventors: Eike Möller; Karl Meng, both of Wuppertal; Egbert Wehinger, Neviges; Harald Horstmann, Wuppertal, all of Germany

[73] Assignee: Bayer Aktiengesellschaft, Germany

[21] Appl. No.: 633,396

[22] Filed: Nov. 19, 1975

Related U.S. Application Data

[62] Division of Ser. No. 461,282, Apr. 15, 1974, Pat. No. 3,957,814.

[30] Foreign Application Priority Data

| Apr. 17, 1973 | Germany | 2319280 |
|---|---|---|
| Dec. 19, 1973 | Germany | 2363139 |

[51] Int. Cl.² ............... C07D 231/20; A61K 31/415
[52] U.S. Cl. .................. 548/367; 424/273 P; 548/363
[58] Field of Search ............. 260/310 A; 424/273

[56] References Cited

U.S. PATENT DOCUMENTS

| 2,376,380 | 5/1945 | Porter et al. | 260/305 |
| 2,476,986 | 7/1949 | Martin | 260/310 R |
| 2,476,987 | 7/1949 | Martin | 260/310 R |
| 2,511,231 | 6/1950 | Weissberger et al. | 96/56.5 |
| 2,600,788 | 6/1952 | Lorin et al. | 95/6 |
| 2,619,419 | 11/1952 | Jennen | 95/6 |
| 2,672,417 | 3/1954 | Jennen | 95/6 |
| 2,681,915 | 6/1954 | Gysin et al. | 260/310 R |
| 2,848,446 | 8/1958 | Moderni | 96/56.5 |
| 2,905,694 | 9/1959 | Pinson, Jr. | 424/273 |
| 3,014,916 | 12/1961 | Wright | 260/310 |
| 3,113,949 | 12/1963 | Bicking | 260/310 |
| 3,153,654 | 10/1964 | Ficken | 260/310 |
| 3,190,888 | 6/1965 | Wolf et al. | 96/56.5 |
| 3,303,200 | 2/1967 | Wolf | 260/310 |
| 3,558,319 | 1/1971 | Hamaoka et al. | 260/310 |
| 3,563,745 | 2/1971 | Eynde et al. | 96/56.5 |
| 3,615,502 | 10/1971 | Yoshida | 260/310 |
| 3,615,506 | 10/1971 | Abbott | 96/565 |
| 3,632,818 | 1/1972 | Allois et al. | 260/310 |
| 3,694,456 | 9/1972 | Noguchi et al. | 260/310 |
| 3,719,764 | 3/1973 | Girault et al. | 424/273 |
| 3,812,145 | 5/1974 | Sato | 260/310 |
| 3,823,156 | 7/1974 | Oku et al. | 260/310 |

FOREIGN PATENT DOCUMENTS

| 727,091 | 7/1969 | Belgium. | |
| 1,584,823 | 1/1970 | France. | |
| 2,068,413 | 8/1971 | France. | |
| 1,003,215 | 7/1957 | Germany. | |
| 2,230,792 | 1/1974 | Germany. | |
| 2,230,675 | 1/1974 | Germany. | |
| 4,742,665 | 12/1972 | Japan. | |
| 599,919 | 3/1948 | United Kingdom. | |
| 779,703 | 7/1957 | United Kingdom. | |
| 961,037 | 6/1964 | United Kingdom. | |
| 1,069,533 | 5/1967 | United Kingdom | 260/310 A |
| 1,190,914 | 5/1970 | United Kingdom. | |

*Primary Examiner*—Donald B. Moyer
*Attorney, Agent, or Firm*—Jacobs & Jacobs

[57] ABSTRACT

1-Substituted pyrazol-5-ones of the formula

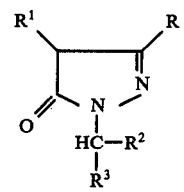

and pharmaceutically acceptable, nontoxic salts thereof, wherein R is hydrogen, amino, alkyl, alkenyl, phenyl or trifluoromethyl;

$R^1$ is hydrogen, alkyl, alkenyl, unsubstituted or substituted aryl or unsubstituted or substituted aralkyl;

$R^2$ is alkyl; and $R^3$ is pyridyl, aryl or substituted by:
 a. 1 or 2 of the same or different substitutents selected from the group consisting of halogen, trifluoromethyl, lower alkyl, lower alkenyl and lower alkoxy;
 b. cycloalkyl of 5, 6 or 7 carbon atoms or cycloalkenyl of 5, 6 or 7 carbon atoms;
 c. mono(lower alkyl)amino, di(lower alkyl)amino, trifluoromethoxy, nitro, cyano, carbamoyl, lower alkylcarbamoyl, di(lower alkyl)carbamoyl, sulphamyl, lower alkylsulphamyl, di(lower alkyl)sulphamyl, or $-SO_n$ lower alkyl wherein $n$ is 0, 1 or 2;
 d. a member selected from the group consisting of mono(lower alkyl)amino, di(lower alkyl)amino, trifluoromethyl, nitro, cyano, carbamoyl, lower alkylcarbamoyl, di(lower alkyl)carbamoyl, sulphamyl, lower alkylsulphamyl, di(lower alkyl) sulphamyl, and $-SO_n$ lower alkyl wherein $n$ is 0, 1 or 2, and 1 or 2 of the same or different substituents selected from the group consisting of lower alkyl, lower alkenyl, lower alkoxy, halogen, and trifluoromethyl; or
 e. a fused, saturated or unsaturated 5-, 6-, or 7- membered ring or said ring containing 1 or 2 oxygen or sulphur atoms;

are useful for their diuretic, saluretic, antihypertensive and antithrombotic effects.

15 Claims, No Drawings

PYRAZOL-5-ONES

CROSS-REFERENCE

This is a division of Ser. No. 461,282 filed Apr. 15, 1974, which is now U.S. Pat. No. 3,957,814.

The present invention relates to 1-substituted pyrazol-5-ones, processes for their production, pharmaceutical compositions useful for effecting diuresis, saluresis and for treating hypertension in humans and animals wherein said 1-substituted pyrazol-5-ones are the active agent, and to methods of effecting diuresis and saluresis in humans and animals and methods of treating hypertension in humans and animals which comprises administering said compounds to such humans or animals.

3-Aminopyrazolones have already been used as color-coupling agents for color photography (A. Weissberger et al., *J. Amer. Chem. Soc.*, 64, 2183 (1942)) and as intermediate products for the preparation of color-coupling agents (British Patent 599,919; U.S. Pat. Nos. 2,367,523; 2,376,380; 2,511,231; 2,600,788; 2,619,419; and 2,672,417).

Certain pyrazol-5-one derivatives are also used as antipyretics, analgesics and antiphlogistics (compare G. Ehrhart and H. Ruschig, *Arzneimittel (Medicines)*, Volume 1, page 148 (1972)).

We have now discovered a new group of 1-substituted pyrazol-5-ones which have strong diuretic, saluretic, antihypertensive and antithrombotic properties.

More particularly, the present invention is concerned with 1-substituted pyrazol-5-ones of the formula

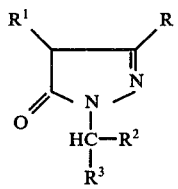

and pharmaceutically acceptable, nontoxic salts thereof, wherein

R is hydrogen, amino, alkyl, preferably lower alkyl, alkenyl, preferably lower alkenyl, phenyl or trifluoromethyl;

$R^1$ is hydrogen, alkyl, preferably lower alkyl, alkenyl, preferably lower alkenyl, unsubstituted or substituted aryl, preferably monoaryl, unsubstituted or substituted by lower alkoxy, or aralkyl, preferably wherein the aryl moiety is a monoaryl moiety and the alkyl moiety is a lower alkyl moiety, said aralkyl being either unsubstituted or substituted by lower alkoxy;

$R^2$ is alkyl, preferably lower alkyl; and $R^3$ is pyridyl; or aryl, preferably aryl of 6 to 10 carbon atoms, substituted by
   a. 1 or 2 of the same or different substituents selected from the group consisting of halogen, trifluoromethyl, lower alkyl, lower alkenyl and lower alkoxy;
   b. cycloalkyl of 5, 6 or 7 carbon atoms or cycloalkenyl of 5, 6 or 7 carbon atoms;
   c. mono(lower alkyl)amino, di(lower alkyl)amino, trifluoromethoxy, nitro, cyano, carbamoyl, lower alkylcarbamoyl, di(lower alkyl)carbamoyl, sulphamyl, lower alkylsulphamyl, di(lower alkyl)sulphamyl, or $-SO_n$ lower alkyl wherein $n$ is 0, 1 or 2;
   d. a member selected from the group consisting of mono(lower alkyl)amino, di(lower alkyl)amino, trifluoromethyl, nitro, cyano, carbamoyl, lower alkylcarbamoyl, di(lower alkyl)carbamoyl, sulphamyl lower alkylsulphamyl, di(lower alkyl)sulphamyl, and $-SO_n$ lower alkyl wherein $n$ is 0, 1 or 2, and 1 or 2 of the same or different substituents selected from the group consisting of lower alkyl, lower alkenyl, lower alkoxy, halogen, and trifluoro methyl; or
   e. a fused, saturated or unsaturated 5-, 6-, or 7-membered ring or said ring containing 1 or 2 oxygen or sulphur atoms;

As used hereinafter, the phrase, "compounds of the present invention," includes both the pyrazol-5-ones and their pharmaceutically acceptable, nontoxic salts.

The compounds of the present invention contain an asymmetric carbon atom which gives rise to optical isomerism. The compounds of the present invention thus include all the optical isomers, as well as the racemates thereof.

In addition to the structure which is represented by formula I above, the compounds of the present invention may also be in one of the following tautomeric forms or in the form of a mixture of such tautomers:

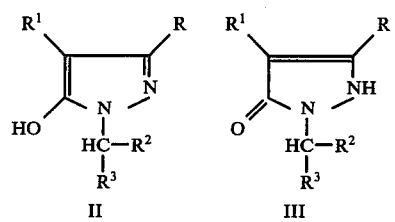

In addition, the 3-amino-pyrazol-5-ones according to the present invention may also be present in the following imino forms:

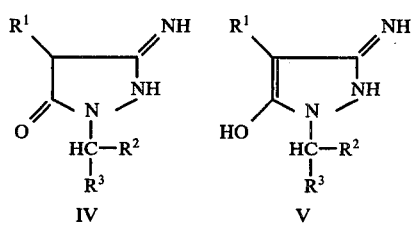

In formulas II, III, IV and V, R, $R^1$, $R^2$ and $R^3$ are as above defined.

The compounds of the present invention may be produced according to the following processes:

A. A hydrazine of the formula

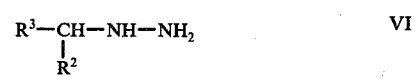

wherein
$R^2$ and $R^3$ are as above defined is reacted with an acetic acid derivative of the formula

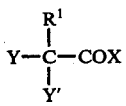

wherein
- R¹ is as above defined,
- X is hydroxy, alkoxy, preferably lower alkoxy, aralkoxy, preferably monoaryllower alkoxy, amino, or alkylamino, preferably lower alkylamino; and either
- Y is hydrogen and
- Y' is cyano, or —COY" wherein Y" is hydrogen, alkyl, preferably lower alkyl, phenyl or trifluoromethyl; or
- Y and Y' together form the moiety

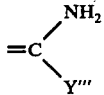

wherein Y''' is alkoxy, preferably lower alkoxy, aryloxy, preferably monoaryloxy, aralkoxy, preferably monoaryl(lower alkoxy), alkylmercapto, preferably lower alkylmercapto, aralkylmercapto, preferably monoaryl(lower alkyl)mercapto, or amino; either in the presence or the absence of an inert solvent and either in the presence or the absence of a basic or acidic catalyst such as an alkaline metal hydroxide, carbonate, or alkaline earth metal hydroxide or carbonate, or hydrogen halide acids, sulphuric acid or sulphonic acids at a temperature of from about 10° C to about 200° C;

B. reacting a compound of the formula:

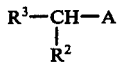

wherein
- R² and R³ are as above defined and
- A is a moiety capable of being cleaved during the course of the reaction, preferably halogen, dialkyloxonium, preferably di(lower alkyl)oxonium, dialkylsulphonium, preferably di(lower alkyl)sulphonium, trialkylammonium, preferably tri(lower alkyl)ammonium, arylsulphonic acid, preferably monoarylsulphonic acid, or trifluoromethylsulphonic acid, with a pyrazol-5-one of the formula

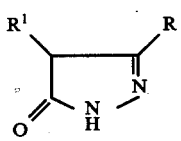

wherein R and R¹ are as above defined either in the presence or the absence of an inert solvent, and either in the presence or the absence of an inorganic or organic base such as an alkali metal hydroxide, carbonate, alcoholate, hydride or amide, at a temperature of from about 10° to about 200° C;

C. when R is amino, reacting a pyrazol-5-one of the formula

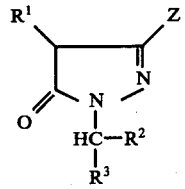

wherein
- R¹, R² and R³ are as above defined, and
- Z is halogen, alkoxy, preferably lower alkoxy, aralkoxy, preferably monoaryl(lower alkoxy), alkylmercapto, preferably (lower alkyl)mercapto, or aralkylmercapto, preferably monoaryl(lower alkyl)mercapto, with ammonia, either in the presence or the absence of an inert solvent at a temperature of from about 20° C to about 220° C;

D. when R is amino, reacting a pyrazol-5-one of the formula

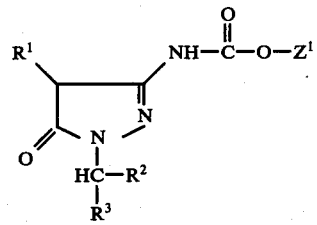

wherein
- R¹, R² and R³ are as above defined, and
- Z¹ is alkyl, preferably lower alkyl, aryl, preferably monoaryl, or aralkyl, preferably monoaryl(lower alkyl), under hydrolization conditions with an acid or base either in the presence or the absence of an inert solvent at a temperature of from about 20° C to about 200° C; or E. when R is hydrogen, lower alkyl or phenyl and R¹ is hydrogen, reacting an acetylenecarboxylic acid of the formula

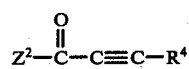

wherein
- R⁴ is hydrogen, lower alkyl or phenyl, and
- Z² is hydroxy, alkoxy, preferably lower alkoxy, aralkoxy, preferably monoaryl(lower alkoxy), amino or alkylamino, preferably (lower alkyl)amino, with a hydrazine of the formula

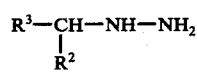

wherein
- R² and R³ are as above defined either in the presence or the absence of an inert solvent and either in the presence or the absence or an inorganic or organic base, at a temperature of from about 50° C to about 200° C.

The five processes A to E above set forth are hereinafter referred to as Process Variants A to E.

The enantiomers of the compounds according to the present invention can be separately prepared according to methods known from the literature (compare, for example, Houben Weyl, *Methoden der organischen Chemie,* IV/2, pages 509 et seq.) by interaction of the racemic forms of the compounds of the invention with a chiral medium, preferably by reaction of the racemate with the derivative of an optically active acid (for example, camphorsulphonic acid, bromocamphorsulphonic acid or quinic acid) or an optically active base (for example, brucine, morphine or strychnine). A mixture of diastereomeric reaction products is thus obtained which can be separated and prepared in a pure form with the aid of physico-chemical methods such as, for example, fractionation, and can subsequently be resolved into optically pure components.

Alternatively, the compounds of the present invention can be prepared in optically active form by producing them by one of the methods described above using optically active precursors. Thus:

(a) an optically pure hydrazine of the formula VI (which can be prepared by known methods) can be reacted with an acetic acid derivative of the formula VII according to Process Variant A; or (b) an optically pure pyrazol-5-one derivative of the formula X (which can also be obtained by known methods) can be reacted with ammonia according to Process Variant C; or (c) an optically pure pyrazol-5-one of the formula XI can be hydrolyzed according to Process Variant D; or (d) an optically pure hydrazine of the formula VI can be reacted with an acetylene-carboxylic acid derivative of the formula XII according to Process Variant E.

The pyrazol-5-ones of formula I and their pharmaceutically acceptable, nontoxic salts can be interconverted according to manners per se known in the art.

Surprisingly, the new compounds of the invention display strong diuretic, saluretic, antithrombotic and antihypertensive actions. Hitherto, diuretic, saluretic, antithrombotic and antihypertensive actions have not been disclosed for the related pyrazol-5-one derivatives known from the prior art, so that the compounds according to the present invention both represent a novel class of compounds and in respect of these specific pharmaceutical actions can be regarded as an enrichment of pharmacy.

Depending on the nature of the starting compounds used, the synthesis of the compounds of the present invention can be illustrated by the following equations, wherein 3-amino-1-(α-methyl-4-chlorobenzyl)-pyrazol-5-one, 3-methyl-1-(α-ethylbenzyl)-pyrazol-5-one, 3,4-dimethyl-1-(α-methyl-3-chlorobenzyl)-pyrazol-5-one, 3-amino-4-methyl-1-(α-ethylbenzyl)-pyrazol-5-one, 3-amino-1-(α-methyl-4-fluorobenzyl)-pyrazol-5-one and 3-methyl-1-(α-methyl-4-chlorobenzyl)-pyrazol-5-one have been chosen as examples and the possible intermediate stages of the reaction sequence, the products of which can at times be isolated, have not been shown.

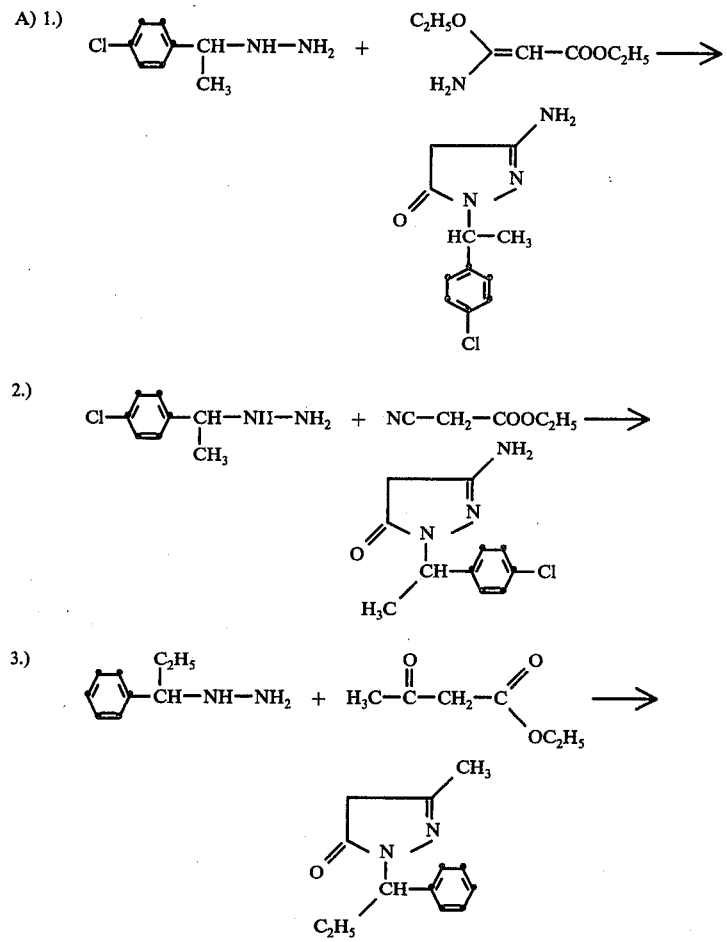

B) 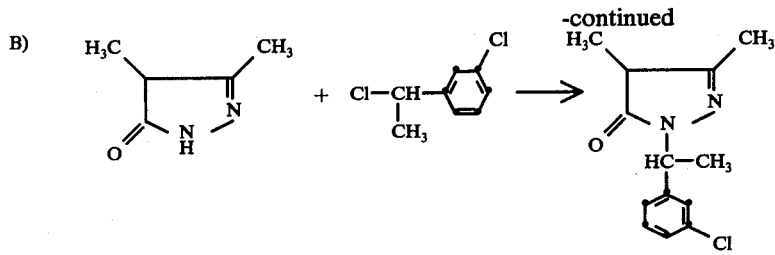

C) 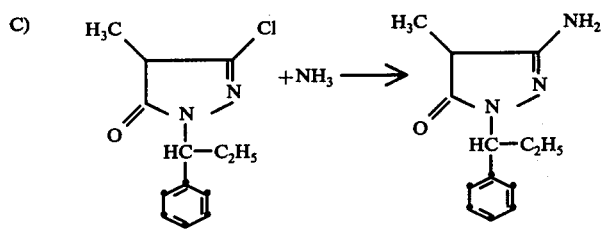

D) 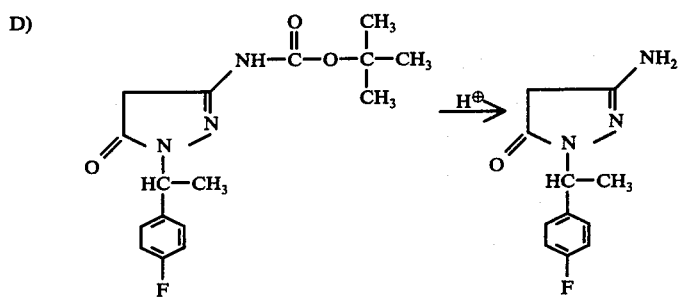

E) 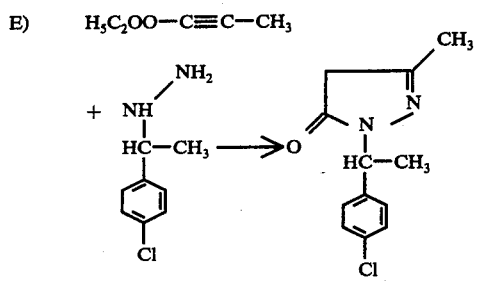

According to one embodiment of the present invention

R is hydrogen, amino, lower alkyl, lower alkenyl, phenyl or trifluoromethyl;

$R^1$ is hydrogen, lower alkyl, lower alkenyl, monoaryl unsubstituted or substituted by lower alkoxy or aralkyl wherein the aryl moiety is a monoaryl moiety and the alkyl moiety is a lower alkyl moiety, said aralkyl being unsubstituted or substituted by lower alkoxy;

$R^2$ is lower alkyl; and $R^3$ is pyridyl; or aryl of 6 to 10 carbon atoms substituted by:

a. 1 or 2 of the same or different substituents selected from the group consisting of halogen, trifluoromethyl, lower alkyl, lower alkenyl and lower alkoxy;

b. monoalkylamino of 1 to 4 carbon atoms in the alkyl moiety, dialkylamino of 1 to 4 carbon atoms in each alkyl moiety, trifluoromethoxy, nitro, cyano, carbamoyl, lower alkylcarbamoyl, di(lower alkylcarbamoyl, sulphamyl, alkylsulphamyl of 1 to 4 carbon atoms in the alkyl moiety, dialkylsulphamyl of 1 to 4 carbon atoms in each alkyl moiety, or —$SO_n$ alkyl wherein n is 0, 1 or 2 and the alkyl moiety has 1 to 4 carbon atoms;

c. a substituent selected from the group consisting of monoalkylamino of 1 to 4 carbon atoms in the alkyl moiety, dialkylamino of 1 to 4 carbon atoms in the alkyl moiety, trifluoromethyl, nitro, cyano, carbamoyl, lower alkylcarbamoyl, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety and —$SO_n$ alkyl wherein n is 0, 1 or 2 and alkyl is of 1 to 4 carbon atoms, and 1 or 2 of the same or different substituents selected from the group consisting of lower alkyl, lower alkenyl, lower alkoxy, halogen and trifluoromethyl; or d. A fused; saturated or unsaturated 5-, 6-, or 7-membered ring or said ring containing 1 or 2 oxygen or sulphur atoms.

According to another embodiment of the present invention

R is hydrogen, amino, lower alkyl, lower alkenyl, or phenyl;

$R^1$ is hydrogen, lower alkyl, lower alkenyl, monoaryl unsubstituted or substituted by lower alkoxy or aralkyl wherein the aryl moiety is a monoaryl moiety and the alkyl moiety is a lower alkyl moiety, said aralkyl being unsubstituted or substituted by lower alkoxy;

$R^2$ is lower alkyl; and $R^3$ is aryl of 6 to 10 carbon atoms substituted by:
  a. 1 or 2 of the same or different substituents selected from the group consisting of halogen, trifluoromethyl, lower alkyl, lower alkenyl and lower alkoxy;
  b. monoalkylamino of 1 to 4 carbon atoms in the alkyl moiety, dialkylamino of 1 to 4 carbon atoms in each alkyl moiety, trifluoromethoxy, nitro, cyano, carbamoyl, lower alkylcarbamoyl, di-(lower alkyl)carbamoyl, sulphamyl, alkylsulphamyl of 1 to 4 carbon atoms in the alkyl moiety, dialkylsulphamyl of 1 to 4 carbon atoms in each alkyl moiety, or —$SO_n$ alkyl wherein $n$ is 0, 1 or 2 and the alkyl moiety has 1 to 4 carbon atoms;
  c. a substituent selected from the group consisting of monoalkylamino of 1 to 4 carbon atoms in the alkyl moiety, dialkylamino of 1 to 4 carbon atoms in the alkyl moiety, trifluoromethyl, nitro, cyano, carbamoyl, carbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety and —$SO_n$ alkyl wherein $n$ is 0, 1 or 2 and alkyl is of 1 to 4 carbon atoms, and 1 or 2 of the same or different substituents selected from the group consisting of lower alkyl, lower alkenyl, lower alkoxy, halogen and trifluoromethyl; or
  d. a fused, saturated or unsaturated 5-, 6-, or 7-membered ring or said ring containing 1 or 2 oxygen or sulphur atoms.

According to another embodiment of the present invention

R is hydrogen, amino, alkyl of 1 to 4 carbon atoms, alkenyl of 2 to 4 carbon atoms, phenyl, or trifluoromethyl;

$R^1$ is hydrogen, alkyl of 1 to 4 carbon atoms, alkenyl of 2 to 4 carbon atoms, phenyl unsubstituted or substituted by alkoxy of 1 to 4 carbon atoms or benzyl unsubstituted or substituted by alkoxy of 1 to 4 carbon atoms;

$R^2$ is alkyl of 1 to 4 carbon atoms;

$R^3$ is pyridyl, naphthyl, or phenyl substituted by:
  a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
  b. monoalkylamino of 1 to 4 carbon atoms, dialkylamino of 1 to 4 carbon atoms, trifluoromethoxy, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety or —$SO_n$ alkyl wherein $n$ is 0, 1 or 2 and alkyl is of 1 to 4 carbon atoms.
  c. a substituent selected from the group consisting of monoalkylamino of 1 to 4 carbon atoms, dialkyl amino of 1 to 4 carbon atoms, trifluoromethyl, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety and —$SO_n$ alkyl wherein $n$ is 0, 1 or 2 and alkyl is of 1 to 4 carbon atoms, and 1 or 2 of the same or different substituents selected from the group consisting of alkyl of 1 to 4 carbon atoms, alkenyl of 2 to 4 carbon atoms, alkoxy of 1 to 4 carbon atoms, halogen and trifluoromethyl; or
  d. a fused, saturated or unsaturated 5-, 6-, or 7-membered ring or said ring containing 1 or 2 oxygen or sulphur atoms.

According to another embodiment of the present invention

R is hydrogen, amino, alkyl of 1 to 4 carbon atoms, alkenyl of 2 to 4 carbon atoms, or phenyl;

$R^1$ is hydrogen, alkyl of 1 to 4 carbon atoms, alkenyl of 2 to 4 carbon atoms, phenyl unsubstituted or substituted by alkoxy of 1 to 4 carbon atoms or benzyl unsubstituted or substituted by alkoxy of 1 to 4 carbon atoms;

$R^2$ is alkyl of 1 to 4 carbon atoms;

$R^3$ is naphthyl, or phenyl substituted by:
  a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
  b. monoalkylamino of 1 to 4 carbon atoms, dialkylamino of 1 to 4 carbon atoms, trifluoromethoxy, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety or —$SO_n$ alkyl wherein $n$ is 0, 1 or 2 and alkyl is of 1 to 4 carbon atoms;
  c. a substituent selected from the group consisting of monoalkylamino of 1 to 4 carbon atoms, dialkyl amino of 1 to 4 carbon atoms, trifluoromethyl, nitro, cyano, carbamoyl, alkylcarbamoyl of 1 to 4 carbon atoms in the alkyl moiety, dialkylcarbamoyl of 1 to 4 carbon atoms in each alkyl moiety, sulphamyl, alkylsulphamyl of 1 to 4 carbon atoms in the alkyl moiety, dialkylsulphamyl of 1 to 4 carbon atoms in each alkyl moiety and —$SO_n$ alkyl wherein $n$ is 0, 1 or 2 and alkyl is of 1 to 4 carbon atoms, and 1 or 2 of the same or different substituents selected from the group consisting of alkyl of 1 to 4 carbon atoms, alkenyl of 2 to 4 carbon atoms, alkoxy of 1 to 4 carbon atoms, halogen and trifluoromethyl; or
  d. a fused, saturated or unsaturated 5-, 6-, or 7-membered ring or said ring containing 1 or 2 oxygen or sulphur atoms.

According to another embodiment of the present invention

R is hydrogen, amino, alkyl of 1 to 4 carbon atoms, phenyl or trifluoromethyl;

$R^1$ is hydrogen, alkyl of 1 to 4 carbon atoms, alkenyl of 2 to 4 carbon atoms, phenyl, benzyl or phenyl or benzyl substituted by alkoxy of 1 or 2 carbon atoms;

$R^2$ is alkyl of 1 to 4 carbon atoms;

$R^3$ is pyridyl; naphthyl; or phenyl substituted by:

a. 1 or 2 straight or branched-chain alkyl moieties of 1 to 8 carbon atoms or alkenyl moieties of 2 to 8 carbon atoms;
b. 1 or 2 alkoxy moieties of 1 to 6 carbon atoms;
c. cycloalkyl of 5, 6 or 7 carbon atoms or cycloalkeny of 5, 6 or 7 carbon atoms;
d. 1 or 2 halogens;
e. 1 or 2 trifluoromethyl moieties;
f. trifluoromethoxy, nitro, cyano or dialkylamino of 1 to 4 carbon atoms in each alkyl moiety;
g. carbamoyl, sulphamyl, mono- or di- alkylcarbamoyl or mono- or di- alkylsulphamyl wherein each alkyl moiety is of 1 to 4 carbon atoms;
h. a moiety of the formula —B, —COB or —SO$_2$B wherein B is a 5-, 6- or 7-membered ring containing a nitrogen atom in the 1-position or said ring which also contains oxygen as a ring member;
i. —SO$_n$ alkyl wherein $n$ is 0 or 2 and alkyl is of 1 to 4 carbon atoms; or
j. a fused, saturated or unsaturated 5-, 6- or 7-membered ring having 1 sulphur atom or 1 or 2 oxygen atoms as ring members.

According to another embodiment of the present invention

R is hydrogen, amino, methyl, ethyl, phenyl or trifluoromethyl;
R$^1$ is hydrogen, alkyl of 1 to 4 carbon atoms, alkenyl of 2 to 4 carbon atoms, phenyl, benzyl, or phenyl or benzyl substituted by alkoxy of 1 or 2 carbon atoms;
R$^2$ is alkyl of 1 to 4 carbon atoms;
R$^3$ is pyridyl; naphthyl; or phenyl substituted by:
a. 1 or 2 straight or branched-chain alkyl moieties of 1 to 4 carbon atoms;
b. 1 or 2 alkoxy moieties of 1 to 4 carbon atoms;
c. cycloalkyl of 5, 6 or 7 carbon atoms or cycloalkenyl of 5, 6 or 7 carbon atoms;
d. 1 or 2 fluoro, chloro or bromo moieties;
e. 1 or 2 trifluoromethyl moieties;
f. trifluoromethoxy, nitro, cyano or dialkylamino of 1 or 2 carbon atoms;
g. carbamoyl, sulphamyl, mono- or di- alkylcarbamoyl or mono- or di- alkylsulphamyl wherein each alkyl moiety is of 1 to 4 carbon atoms;
h. —SO$_n$ alkyl wherein $n$ is 0 or 2 and alkyl is of 1 to 4 carbon atoms; or
i. a fused, saturated, 6-membered ring.

According to another embodiment of the present invention

R is hydrogen, amino, methyl, ethyl or phenyl;
R$^1$ is hydrogen, alkyl of 1 to 4 carbon atoms, alkenyl of 2 to 4 carbon atoms, phenyl, benzyl, or phenyl or benzyl substituted by alkoxy of 1 or 2 carbon atoms;
R$^2$ is alkyl of 1 to 4 carbon atoms;
R$^3$ is naphthyl; or phenyl substituted by:
a. 1 or 2 straight or branched-chain alkyl moieties of 1 to 4 carbon atoms;
b. 1 or 2 alkoxy moieties of 1 to 4 carbon atoms;
c. cycloalkyl of 5, 6 or 7 carbon atoms or cycloalkenyl of 5, 6 or 7 carbon atoms;
d. 1 or 2 fluoro, chloro or bromo moieties;
e. 1 or 2 trifluoromethyl moieties;
f. trifluoromethoxy, nitro, cyano or dialkylamino of 1 or 2 carbon atoms;
g. carbamoyl, sulphamyl, mono- or di- alkylcarbamoyl or mono- or di- alkylsulphamyl wherein each alkyl moiety is of 1 to 4 carbon atoms;
h. —SO$_n$ alkyl wherein $n$ is 0 or 2 and alkyl is of 1 to 4 carbon atoms; or
i. a fused, saturated, 6-membered ring.

Another preferred embodiment of the present invention is

R is hydrogen, amino, alkyl of 1 to 3 carbon atoms, phenyl or trifluoromethyl;
R$^1$ is hydrogen or alkyl of 1 or 2 carbon atoms;
R$^2$ is alkyl of 1 to 3 carbon atoms; and
R$^3$ is pyridyl; naphthyl; or phenyl substituted by fluorine, chlorine, bromine, iodine, trifluoromethyl, trifluoromethoxy, nitro, cyano, alkyl of 1 to 4 carbon atoms, sulphamyl, dimethylamino, alkoxy of 1 to 4 carbon atoms, dichlorine, chlorine and methyl, chlorine and bromine, chlorine and fluorine, chlorine and sulphamyl, chlorine and trifluoromethyl, chlorine and methoxy, difluorine, di(difluoromethyl), fluorine and methyl, trifluoromethyl and methoxy, di(trifluoromethyl), dimethyl, methyl and trifluoromethyl or by a 6-membered, fused, saturated ring.

Another preferred embodiment of the present invention is

R is hydrogen, amino, alkyl or 1 to 3 carbon atoms or trifluoromethyl;
R$^1$ is hydrogen or alkyl of 1 or 2 carbon atoms;
R$^2$ is alkyl of 1 to 3 carbon atoms; and
R$^3$ is naphthyl; or phenyl substituted by fluorine, chlorine, bromine, iodine, trifluoromethyl, trifluoromethoxy, nitro, cyano, alkyl of 1 to 4 carbon atoms, sulphamyl, dimethylamino, alkoxy of 1 to 4 carbon atoms, dichlorine, chlorine and methyl, chlorine and bromine, chlorine and fluorine, chlorine and sulphamyl, chlorine and trifluoromethyl, chlorine and methoxy, difluorine, di(difluoromethyl), fluorine and methyl, trifluoromethyl and methoxy, di(trifluoromethyl), dimethyl, methyl and trifluoromethyl or by a 6-membered, fused, saturated ring.

Another preferred embodiment of the present invention is

R is amino, alkyl of 1 or 2 carbon atoms, phenyl or trifluoromethyl;
R$^1$ is hydrogen, alkyl of 1 to 3 carbon atoms, phenyl, benzyl or methoxybenzyl;
R$^2$ is alkyl of 1 or 2 carbon atoms; and
R$^3$ is naphthyl; pyridyl; or phenyl substituted by chlorine, fluorine, bromine, methyl, dichlorine or chlorine and methyl.

Another preferred embodiment of the present invention is

R is amino, methyl, phenyl or trifluoromethyl;
R$^1$ is hydrogen, methyl, ethyl, propyl, phenyl, benzyl or methoxybenzyl;
R$^2$ is methyl; and
R$^3$ is naphthyl; pyridyl; or phenyl substituted by fluorine, bromine, methyl, dichlorine or chlorine and methyl.

Another preferred embodiment of the present invention is

R is amino, methyl or phenyl;
R$^1$ is hydrogen, methyl, ethyl, propyl, phenyl, benzyl or methoxybenzyl;
R$^2$ is methyl; and
R$^3$ is naphthyl; or phenyl substituted by fluorine, bromine, methyl, dichlorine or chlorine and methyl.

According to Process Variant A

X is preferably hydroxy, lower alkoxy, especially alkoxy of 1 to 4 carbon atoms, aralkoxy, especially lower alkoxyphenyl, amino, or lower alkylamino, especially alkylamino of 1 to 4 carbon atoms, and Y is hydrogen and Y' is cyano, or —COY" wherein Y" is hydrogen, lower alkyl, especially alkyl of 1 to 4 carbon atoms, phenyl or trifluoromethyl; or Y and Y' together form the moiety

wherein Y'" is lower alkoxy, especially alkoxy of 1 to 4 carbon atoms, aryloxy, especially phenoxy, aralkoxy, especially lower alkoxyphenyl, alkylmercapto, especially lower alkylmercapto and particularly alkylmercapto of 1 to 4 carbon atoms, aralkylmercapto, especially benzylmercapto of 1 to 4 carbon atoms in the alkyl moiety, or amino.

The hydrazines of formula VI which are used as starting materials according to Process Variant A are known in the literature or can be prepared by methods which are per se known. (Compare, for example, Hoben-Weyl's *Methoden der organischen Chemie* (Methods of Organic Chemistry), Volume X, 2, page 6.)

Representative hydrazines of the formula VI include:

α-methyl-3-chlorobenzylhydrazine,
α-methyl-3-bromobenzylhydrazine,
α-methyl-4-chlorobenzylhydrazine,
α-methyl-4-bromobenzylhydrazine,
α-methyl-3,4-dichlorobenzylhydrazine,
α-methyl-3,4-dibromobenzylhydrazine,
α-methyl-3-bromo-4-chlorobenzylhydrazine,
α-methyl-4-bromo-3-chlorobenzylhydrazine,
α-methyl-4-methylbenzylhydrazine,
α-methyl-3-methylbenzylhydrazine,
α-methyl-3-ethylbenzylhydrazine,
α-methyl-4-trifluoromethylbenzylhydrazine,
α-methyl-4-chloro-3-methylbenzylhydrazine,
α-methyl-4-methyl-3-trifluoromethylbenzylhydrazine,
α-methyl-3-chloro-4-trifluoromethylbenzylhydrazine,
α-methyl-4-chloro-3-trifluoromethylbenzylhydrazine,
α-methyl-4-sulphonamidobenzylhydrazine,
α-methyl-4-chloro-3-sulphonamidobenzylhydrazine,
α-methyl-4-methoxybenzylhydrazine,
α-(naphthyl-(2))-ethylhydrazine,
α-methyl-3,4-tetramethylenebenzylhydrazine,
α-methyl-3,4-methylenedioxybenzylhydrazine,
α-ethyl-4-chlorobenzylhydrazine,
α-ethyl-3-chlorobenzylhydrazine,
α-ethyl-1,4-dichlorobenzylhydrazine,
α-ethyl-4-bromo-3-chlorobenzylhydrazine and
α-ethyl-3-chloro-4-methylbenzylhydrazine.

Acetic acid derivatives of the formula VII, which are used as starting materials, are known from the literature or can be prepared by processes known from the literature (compare *Org. Synth.*, Coll. I, 249; *Org. Synth.*, 41, 50; Cope, *J. Amer. Chem. Soc.*, 67, 1047 (1945); C. C. Steele, *J. Amer. Chem. Soc.*, 53, 286 (1931); A. H. Cook, *J. Chem. Soc.* (London) 1949, 3224).

Although referred to in this specification as acetic acid derivatives, the compounds of formula VII can perhaps more accurately be designated as β-aminoacrylic acid derivatives when Y and Y' together form the moiety

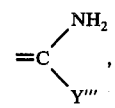

cyanoacetic acid derivatives when Y is hydrogen and Y' is cyano, or as β-ketoacid derivatives when Y is hydrogen and Y' is

Representative acetic acid derivatives of the formula VII include:

cyanoacetic acid methyl ester,
cyanoacetic acid ethyl ester,
cyanoacetic acid propyl ester,
cyanoacetic acid isopropyl ester,
cyanoacetic acid n-butyl ester (compare Org. Synth. 41, page 5
cyanoacetic acid isobutyl ester,
cyanoacetic acid t-butyl ester,
cyanoacetic acid hexyl ester,
cyanoacetic acid benzyl ester,
cyanoacetic acid amide,
cyanoacetic acid methylamide,
cyanoacetic acid diethylamide,
cyanoacetic acid butylamide,
α-cyanopropionic acid methyl ester,
α-cyanopropionic acid n-butyl ester,
α-cyanopropionic acid ethyl ester,
α-cyanopropionic acid propyl ester,
α-cyanopropionic acid isopropyl ester,
α-cyanopropionic acid isobutyl ester,
α-cyanopropionic acid t-butyl ester,
α-cyanopropionic acid hexyl ester,
α-cyanopropionic acid benzyl ester,
α-cyanopropionic acid amide,
α-cyanopropionic acid methylamide,
α-cyanopropionic acid diethylamide,
α-cyanopropionic acid butylamide,
α-cyanobutyric acid ethyl ester,
α-cyanobutyric acid t.-butyl ester,
α-cyanobutyric acid diethylamide,
β-amino-β-methoxyacrylic acid ethyl ester,
β-amino-β-ethoxyacrylic acid ethyl ester,
β-amino-β-butoxyacrylic acid butyl ester,
β-amino-β-phenoxyacrylic acid ethyl ester,
β-amino-β-benzyloxyacrylic acid benzyl ester,
β-amino-β-ethoxyacrylic acid amide,
β-amino-β-ethoxyacrylic acid diethylamide,
β-amino-β-methylmercaptoacrylic acid ethyl ester,
β-amino-β-benzylmercaptoacrylic acid ethyl ester,
β-amino-β-methylmercaptoacrylic acid amide,
β,β-diaminoacrylic acid ethyl ester,
β,β-diaminoacrylic acid amide,
β-amino-β-methoxymethacrylic acid ethyl ester,
β-amino-β-ethoxymethacrylic acid ethyl ester,
β-amino-β-butoxymethacrylic acid butyl ester,
β-amino-β-phenoxymethacrylic acid ethyl ester,
β-amino-β-benzyloxymethacrylic acid ethyl ester, β-amino-β-methylmercaptomethacrylic acid ethyl ester,
β-amino-β-benzylmercaptomethacrylic acid ethyl ester,
β-amino-β-ethoxymethacrylic acid amide,
β-amino-β-ethoxymethacrylic acid diethylamide,
β-amino-β-methylmercaptomethacrylic acid amide,
β,β-diaminomethacrylic acid ethyl ester,
β,β-diaminomethacrylic acid amide,
β-amino-β-ethoxy-α-ethylacrylic acid ethyl ester,
β-amino-β-methylmercapto-α-ethylacrylic acid ethyl ester,
β-amino-β-ethoxy-α-ethylacrylic acid amide,
β-amino-β-ethoxy-α-phenylacrylic acid ethyl ester,
βamino-β-ethoxy-α-benzylacrylic acid ethyl ester,
α-formylacetic acid ethyl ester,
α-formylpropionic acid ethyl ester,
acetoacetic acid ethyl ester,
acetoacetic acid n-butyl ester,
acetoacetic acid isopropyl ester,
acetoacetic acid t-butyl ester,
acetoacetic acid diethylamide,
propionylacetic acid ethyl ester,
propionylacetic acid isopropyl ester,
propionylacetic acid n-butyl ester,
benzoylacetic acid ethyl ester,
α-acetylpropionic acid ethyl ester,
α-acetylpropionic acid n-butyl ester,
α-acetylpropionic acid t-butyl ester,
α-propionylpropionic acid ethyl ester,
α-propionylpropionic acid isopropyl ester,
α-acetylbutyric acid ethyl ester,
α-propionylbutyric acid ethyl ester,
α-propionylbutyric acid isopropyl ester,
α-benzoylacetoacetic acid ethyl ester and
ω,ω,ω-trifluoroacetoacetic acid ethyl ester.

Diluents for use according to Process Variant A include all inert organic solvents, which, when they are miscible with water, can also, if desired, be diluted with water. Preferred organic solvents include hydrocarbons (such as benzene, toluene and xylene), halogenated hydrocarbons (such as methylene chloride, chloroform, carbon tetrachloride and chlorobenzene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide, dimethylacetamide, N-methylpyrrolidone and hexamethylphosphoric acid triamide), sulphoxides (such as dimethylsulphoxide), sulphones (such as sulpholane) and bases (such as pyridine, picoline, collidine, lutidine and quinoline).

As basic condensation agents in Process Variant A there may be used inorganic and organic bases. Preferred bases for this purpose include alkali metal hydroxides (such as sodium hydroxide and potassium carbonate) and alcoholates (such as sodium alcoholate and potassium alcoholate).

Alternatively there may be used as an acid catalyst, inorganic or organic acid. Preferred acids include hydrogen halide acids, sulphuric acid and sulphonic acids (such as toluenesulphonic acid and trifluoromethylsulphonic acid).

The reaction temperatures in Process Variant A can be varied over a substantial range. In general, the reaction is carried out at a temperature of from 10° C to about 200° C, preferably between 20° C and 100° C. It can be carried out under atmospheric pressure but also in closed vessels at a higher pressure.

In carrying out the process according to the invention, as illustrated by equation A 1), 1 mol of the hydrazine VI and 1 mol of β-aminoacrylic acid derivative VII (Y and Y' together are

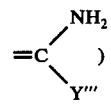

are reacted. It is possible to start either from the β-aminoacrylic acid derivative in the free form or from its acid addition salts. In the latter case it is desirable to add 1 mol of a base in order to liberate the β-aminoacrylic acid derivative. If the hydrazine derivative and the β-aminoacrylic acid derivative are employed in the free form, the addition of 1 to 10% of an acid catalyst is desirable. Another possible procedure is to add a correspondingly smaller amount of a base to the reaction mixture for the purpose of neutralizing the salt of β-aminoacrylic acid derivative. When using the acid addition salt, the reaction can also be carried out by isolating the intermediate amidrazone of the formula:

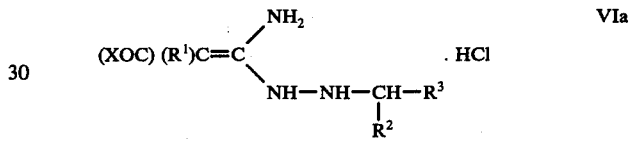

which are first produced and then cyclizing these in a second reaction step, thermally or by the action of a basic condensation agent, to give the compounds of the invention. However, the one-stage synthesis is particularly advantageous.

In carrying out the process according to the invention as illustrated in equation A 2), 1 mol of the cyanoacetic acid derivative VII (Y is H, Y' is cyano), and 1 to 3 mols, preferably 2 mols, of the basic condensation agent are employed per 1 mol of the hydrazine VI. With this procedure, the compounds of the present invention are obtained in the form of their salts and can be liberated by treatment with equivalent amounts of a dilute acid. They can easily be purified by recrystallization from a suitable solvent or by dissolving them with dilute sodium hydroxide solution, filtering the solution in the presence of animal charcoal and precipitating the product by means of dilute acids.

If the process according to the present invention is carried out as illustrated in reaction scheme A 3), 1 mol of the hydrazine derivative VI is reacted with 1 mol of the β-ketoacid derivative VII (Y is hydrogen, Y' is

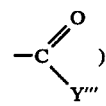

in a suitable diluent, the reaction mixture preferably being stirred for two hours at an elevated temperature after completion of the exothermic initial reaction. The compounds of the present invention, which in most cases are obtained in a crystalline form can easily be purified by recrystallization from a suitable solvent.

According to Process Variant B, A is preferably chlorine or bromine. The halogen compounds of formula VIII used in Process Variant B as starting substances are known from the literature or can be prepared by methods known from the literature (compare, for example, Houben-Weyl, *Methoden der organischen Chemie* (Methods of Organic Chemistry), Volume V, 3 (1962) and Volume V, 4 (1960)). The following halogen compounds VIII which are representative of the starting materials which can be used according to the present process include:

α-methyl-3-chlorobenzyl chloride,
α-methyl-3-bromobenzyl chloride,
α-methyl-4-chlorobenzyl chloride,
α-methyl-4-bromobenzyl chloride,
α-methyl-3,4-dichlorobenzyl chloride,
α-methyl-4-bromo-3-chlorobenzyl chloride,
α-methyl-4-methylbenzyl chloride,
α-methyl-4-trifluoromethylbenzyl chlorides,
α-methyl-3-chloro-4-methylbenzyl chloride,
α-methyl-4-chlorobenzyl bromide,
α-methyl-3,4-dichlorobenzyl bromide,
α-methyl-3-chloro-4-methylbenzyl bromide,
α-ethyl-3,4-dichlorobenzyl chloride and
α-ethyl-3-chloro-4-methylbenzyl chloride.

The pyrazol-5-one derivatives of the formula IX used as starting compounds in Process Variant B are known from the literature or can be prepared by methods known from the literature (compare, for example, B. Graham et al., *J. Amer. Chem. Soc.*, 71, 983 (1949); R. Jones et al. *Tetrahedron,* 19, 1947 (1963)).

Representative pyrazol-5-ones of formula IX which can be used according to the process of the present invention include:

3-methyl-pyrazol-5-one,
3-ethylpyrazol-5-one,
3-trifluoromethylpyrazol-5-one,
3,4-dimethylpyrazol-5-one,
3-methyl-4-phenylpyrazol-5-one,
3-methyl-4-benzylpyrazol-5-one,
3-amino-pyrazol-5-one,
3-amino-4-methylpyrazol-5-one and
3-amino-4-phenylpyrazol-5-one.

Possible diluents for use in Process Variant B are all inert solvents. Preferred solvents include hydrocarbons (such as benzene, toluene and xylene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide and dimethylacetamide, N-methylpyrrolidone, and hexamethylphosphoric acid triamide), sulphoxides (such as dimethylsulphoxide) and sulphones (such as sulpholane).

Bases which can be used in Process Variant B include in principle, all inorganic and organic ides, carbonates, alcoholates, hydrides and amides.

The reaction temperatures in Process Variant B can be varied over a substantial range. Preferably, the reaction is carried out at a temperature of from 20° C to about 120° C. It is generally carried out under atmospheric pressure but one can also carry it out in a closed vessel at a higher pressure.

In carrying out Process Variant B, a salt is generally first prepared from one mol of the pyrazolone derivative IX in a suitable solvent by means of an equimolar amount of a base. One mol of the halogen compound is added to a solution of this salt and the entire reaction mixture is stirred, preferably at an elevated temperature.

The compounds of the present invention are preferably isolated by distilling off the solvent in vacuo, taking up the residue in water and rendering the aqueous mixture weakly acid. The compounds of the present invention obtained using this procedure can easily be purified by recrystallization from a suitable solvent.

According to Process Variant C, Z is preferably chlorine or bromine.

The pyrazol-5-one derivatives of formula X used as starting compounds in Process Variant C can be prepared in a simple manner by methods known from the literature (compare, for example, Japanese Patent 2872 ('64) (1961) and G. Barnikow, Chem. Ber., 100, 1661 (1967)).

The following pyrazole-5-ones of formula X, wherein Z is chlorine or bromine, are representative of those which can be used according to the process of the present invention:

3-chloro-1-(α-methyl-4-chlorobenzyl)-pyrazol-5-one,
3-chloro-1-(α-methyl-4-bromobenzyl)-pyrazol-5-one,
3-chloro-1-(α-methyl-3,4-dichlorobenzyl)-pyrazol-5-one,
3-chloro-1-(α-methyl-4-bromo-3-chlorobenzyl)-pyrazol-5-one,
3-chloro-1-(α-methyl-3-chloro-4-methylbenzyl)-pyrazol-5-one,
3-bromo-1-(α-methyl-4-bromo-3-chlorobenzyl)-pyrazol-5-one,
3-bromo-1-(α-methyl-3-chloro-4-methylbenzyl)-pyrazol-5-one,
3-chloro-1-(α-ethyl-3,4-dichlorobenzyl)-pyrazol-5-one,
3-chloro-1-(α-ethyl-3-chloro-4-methylbenzyl)-pyrazol-5-one,
3-chloro-4-methyl-1-(α-methyl-3,4-dichlorobenzyl)-pyrazol-5-one,
3-chloro-4-methyl-1-(α-methyl-4-bromo-3-chlorobenzyl)-pyrazol-5-one, and
3-chloro-4-phenyl-1-(α-methyl-3,4-dichlorobenzyl)-pyrazol-5-one.

Possible diluents for use in Process Variant C are water and all inert organic solvents which, where they are water-miscible, can be diluted with water. Preferred organic solvents include hydrocarbons (such as benzene, toluene and xylene), alcohols (such as methanol, ethanol, propanol, butanol, benzyl alcohol and glycol monomethyl ether), and ethers (such as tetrahydrofuran, dioxane and glycol dimethyl ether).

The reaction temperatures in Process Variant C can be varied over a substantial range. The reaction is generally carried out at a temperature of from about 20° C to 220° C, but preferably between 50° C and 150° C. It can be carried out either under atmospheric pressure or in closed vessels at higher pressures.

In carrying out Process Variant C, one mol of the pyrazolone derivative X is generally reacted with a twofold to twenty-fold, preferably tenfold, excess of ammonia.

The procedure followed is preferably that the reactants, optionally in an inert solvent, are reacted in a closed vessel at an elevated temperature. The compounds of the present invention, thus obtained, can easily be purified by recrystallization from a suitable solvent.

According to Process Variant D, $Z^1$ is preferably straight or branched-chain alkyl of 1 to 6 carbon atoms, especially t-butyl, or a phenyl or benzyl. The pyrazol-5-one of formula XI is hydrolyzed with an inorganic or organic acid such as a hydrogen halode acid, sulphuric acid, phosphoric acid, acetic acid, trifluoroacetic acid or a mixture of two or more thereof with a base such as an alkali metal hydroxide or alkali earth metal hydroxide as above described.

The pyrazol-5-one derivatives of the formula XI used as starting compounds have not hitherto been disclosed but can be prepared by methods known from the literature, for example, by reacting the carboxylic acid of the formula XIII, wherein $R^1$, $R^2$ and $R^3$ are as above defined,

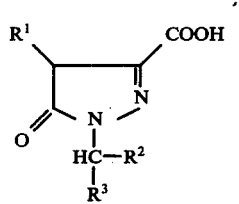

XIII which in turn can be obtained by hydrolysis of the corresponding esters which can be prepared from optionally substituted oxalacetic acid esters and hydrazines of the formula VI according to a modified Curtius reaction with diphenylphosphoryl azide (T. Shioiri et al., *J. Amer. Chem. Soc.*, 94, 6203 (1972)) or by Weinstock's method (*J. Org. Chem.*, 26, 3511 (1961)).

The following pyrazol-5-ones of the formula XI are representative of those which may be used according to the process of the present invention:

3-carboethoxyamino-1-(α-methyl-4-chlorobenzyl)-pyrazol-5-one,
3-carboethoxyamino-1-(α-methyl-4-bromobenzyl)-pyrazol-5-one,
3-carboethoxyamino-1-(α-methyl-3,4-dichlorobenzyl)-pyrazol-5-one,
3-carbo-t-butoxyamino-1-(α-methyl-3,4-dichlorobenzyl)-pyrazol-5-one,
3-carboethoxyamino-1-(α-methyl-4-bromo-3-chlorobenzyl)-pyrazol-5-one,
3-carbopropoxyamino-1-(α-ethyl-3,4-dichlorobenzyl)-pyrazol-5-one,
3-carbo-t-butoxyamino-1-(α-methyl-4-bromo-3-chlorobenzyl)-pyrazol-5-one,
3-carbo-t-butoxyamino-1-(α-methyl-3-chloro-4-methylbenzyl)-pyrazol-5one,
3-carbophenoxyamino-1-(α-methyl-3,4-dichlorobenzyl)-pyrazol-5-one, and
3-carbobenzyloxyamino-1-(α-methyl-3,4-dichlorobenzyl)-pyrazol-5-one.

Possible diluents for use in Process Variant D are water and water-miscible inert organic solvents. Preferred solvents include alcohols (such as methanol, ethanol, propanol, ethylene glycol and glycol monomethyl ether), and ethers (such as tetrahydrofuran or dioxane).

The reaction temperatures in Process Variant D can be varied over a substantial range. Preferably, the reaction is carried out at a temperature of from about 70° C to about 150° C. Normally the reaction is carried out under atmospheric pressure, but it can also be carried out in closed vessels at higher pressure.

In carrying out Process Variant D, an aliquot part of the pyrazolone derivative XI, optionally in an inert solvent, is generally stirred with, preferably, a 5-fold to 25-fold excess of an aqueous solution of an acid or a base at an elevated temperature. The compounds of the present invention precipitate after neutralization of the reaction solution and can easily be purified by recrystallization from a suitable solvent.

According to Process Variant E, $R^2$ is preferably hydroxy, straight or branched-chain alkoxy of 1 to 6 carbon atoms, especially methoxy or ethoxy, benzyloxy or amino or alkylamino or dialkylamino of 1 to 4 carbon atoms in each alkyl moiety and $R^4$ is preferably hydrogen, alkyl of 1 to 4 carbon atoms or phenyl.

The acetylenecarboxylic acid derivatives of the formula XII used as starting compounds in Process Variant E are known from the literature or can be prepared by methods known from the literature. (Compare, for example, Beilstein's *Handbuch der organischen Chemie* (Handbook of Organic Chemistry 2, III, 1,447 et seq. (1961) and 9, III, 3,061 et seq (1971))

Representative acetylenecarboxylic acids of the formula XII which may be used according to the process of the present invention include:

propiolic acid ethyl ester,
propiolic acid n-butyl ester,
propiolic acid iso-propyl ester,
propiolic acid benzyl ester,
propiolic acid amide,
propiolic acid dimethylamide,
propiolic acid ethylamide,
tetrolic acid ethyl ester.
tetrolic acid n-propyl ester,
tetrolic acid isopropyl ester,
phenylpropiolic acid ethyl ester,
phenylpropiolic acid n-butyl ester,
phenylpropiolic acid iso-propyl ester,
phenylpropiolic acid benzyl ester,
phenylpropiolic acid amide,
phenylpropiolic acid ethylamide and
phenylpropiolic acid dimethylamide.

The hydrazines VI used in Process Variant E are the same as those used in Process Variant A, q.v.

Possible diluents for use in Process Variant E are all inert organic solvents which, where they are water-miscible, can be diluted with water. Preferred organic solvents include hydrocarbons (such as benzene, toluene and xylene), halogenated hydrocarbons (such as methylene chloride, chloroform, carbon tetrachloride and chlorobenzene), alcohols (such as methanol, ethanol, propanol, butanol, benzyl alcohol and glycol monomethyl ether), ethers (such as tetrahydrofuran, dioxane and glycol dimethyl ether), amides (such as dimethylformamide, dimethylacetamide, N-methyl-pyrrolidone and hexamethylphosphoric acid triamide), sulphoxides (such as dimethylsulphoxide), sulphones (such as sulpholane) and bases (such as pyridine, picoline, collidine, lutidine and quinoline).

Possible basic condensation agents for use in Process Variant E are inorganic and organic bases. Preferred condensation agents include alkali metal hydroxides and carbonates (such as sodium hydroxide and potassium carbonate) and alcoholates (such as sodium alcoholate and potassium alcoholate).

The reaction temperatures in Process Variant E can be varied within a substantial range. In general, the reaction is carried out at a temperature of from about 50° C to about 200° C, preferably between 70° C and 150° C. It is carried out under atmospheric pressure but can also be carried out in closed vessels at a higher pressure.

In carrying out Process Variant E, 1 mol of the acetylenecarboxylic acid derivative XII, optionally in a suitable diluent, is generally reacted with 1 mol of the hydrazine VI. The compounds of the present invention, which, in most cases, are obtained in a crystalline form, if necessary after evaporating off the diluent, can easily be purified by recrystallization from a suitable solvent.

The quantities of mentioned in Process Variants A to E can, of course, be varied slightly.

The following compounds are representative of those of the present invention:

3-amino-4-methyl-1-(α-methyl-3-chlorobenzyl)-pyrazol-5-one,
3-amino-4-methyl-1-(α-methyl-3,4-dichlorobenzyl)-pyrazol-5-one,
3-amino-4-methyl-1-(α-methyl-3-chloro-4-methylbenzyl)-pyrazol-5-one,
3-amino-4-methyl-1-(α-methyl-4-trifluoromethylbenzyl)-pyrazol-5-one,
3-amino-4-methyl-1-(α-methyl-3-chloro-4-bromobenzyl)-pyrazol-5-one,
3-amino-4-methyl-1-(α-(naphthyl-(2))-ethyl)-pyrazol-5-one,
3-amino-4-methyl-1-(α-methyl-3-fluorobenzyl)-pyrazol-5-one*,
3-amino-4-methyl-1-(α-methyl-4-fluorobenzyl)-pyrazol-5-one*,
3-amino-4-methyl-1-(α-methyl-3,4-difluorobenzyl)-pyrazol-5-one*,
3-amino-4-methyl-1-(α-methyl-3-chloro-4-fluorobenzyl)-pyrazol-5-one*,
3-amino-4-methyl-1-(α-methyl-3,4-di-(fluoromethyl)-benzyl)-pyrazol-5-one*,
3-amino-4-methyl-1-(α-methyl-3,4-tetramethylenebenzyl)-pyrazol-5-one*,
3-amino-4-methyl-1-(α-methyl-2,3-tetramethylenebenzyl)-pyrazol-5-one*,
3-amino-4-methyl-1-(α-(4-pyridyl)-ethyl)-pyrazol-5one*,
3-amino-4-methyl-1-(α-(3-pyridyl)-ethyl)-pyrazol-5-one*,
3,4-dimethyl-1-(α-methyl-4-chlorobenzyl)-pyrazol-5-one,
3,4-dimethyl-1-(α-methyl-3-chloro-4-methylbenzyl)-pyrazol-5-one,
3,4-dimethyl-1-(α-methyl-4-bromo-3-chlorobenzyl)-pyrazol-5-one,
3,4-dimethyl-1-(α-methyl-4-trifluoromethylbenzyl)-pyrazol-5-one,
3,4-dimethyl-1-(α-(naphthyl-(2))-ethyl)-pyrazol-5-one,
1-(α-methyl-3,4-dichlorobenzyl)-pyrazol-5-one,
3-amino-1-(α-methyl-3-chlorobenzyl)-pyrazol-5-one,
3-amino-1-(α-methyl-3-bromobenzyl)-pyrazol-5-one,
3-amino-1-(α-methyl-3-fluorobenzyl)-pyrazol-5-one,
3-amino-1-(α-methyl-4-fluorobenzyl)-pyrazol-5-one,
3-amino-1-(α-methyl-4-chlorobenzyl)-pyrazol-5-one,
3-amino-1-(α-methyl-4-iodobenzyl)-pyrazol-5-one,
3-amino-1-(α-methyl-4-trifluoromethylbenzyl)-pyrazol-5-one,
3-amino-1-(α-methyl-4-trifluoromethoxybenzyl)-pyrazol-5-one,
3-amino-1-(α-methyl-3-trifluoromethyl-4-methoxybenzyl)-pyrazol-5-one,
3amino-1-(α-methyl-3-chloro-4-bromobenzyl)-pyrazol-5-one,
3-amino-1-(α-methyl-4-chloro-3-sulphonamidobenzyl)-pyrazol-5-one,
3-amino-1-(α-(naphthyl-(2))-ethyl)-pyrazol-5-one,
3-amino-1-(α-ethyl-4-nitrobenzyl)-pyrazol-5-one,
3-amino-1-(α-ethyl-4-cyanobenzyl)-pyrazol-5-one,
3-amino-1-(α-n-propyl-2-chloro-4-fluorobenzyl)-pyrazol-5-one,
3-amino-1-(α-methyl-3,4-difluorobenzyl)-pyrazol-5-one*,
3-amino-1-(α-methyl-3,4-di-(trifluoromethyl)-benzyl)-pyrazol-5-one*,
3-amino-1-(α-(4-pyridyl)-ethyl)-pyrazol-5-one*,
3-amino-1-(α-(3-pyridyl)-ethyl)-pyrazol-5-one*,
3-amino-1-(α-methyl-3,4-tetramethylenebenzyl)-pyrazol-5-one*,
3-amino-1-(α-methyl-2,3-tetramethylenebenzyl)-pyrazol-5-one*,
3-methyl-1-(α-methyl-4-butylbenzyl)-pyrazol-5-one,
3-methyl-1-(α-methyl-3-trifluoromethyl-4-chlorobenzyl)-pyrazol-5-one,
3-methyl-1-(α-methyl-4-sulphonamidobenzyl)-pyrazol-5-one,
3-methyl-1-(α-methyl-4-dimethylaminobenzyl)-pyrazol-5-one,
3-methyl-1-(α-methyl-3,4-tetramethylenebenzyl)-pyrazol-5-one,
3-methyl-1-(α-methyl-3-chlorobenzyl)-pyrazol-5-one,
3-methyl-1-(α-methyl-2-chlorobenzyl)-pyrazol-5-one,
3-methyl-1-(α-methyl-3,5-dichlorobenzyl)-pyrazol-5-one,
3-methyl-1-(α-methyl-3-fluorobenzyl)-pyrazol-5-one,
3-methyl-1-(α-methyl-4-chloro-3-bromobenzyl)-pyrazol-5-one,
3-methyl-1-(α-methyl-4-fluoro-3-chlorobenzyl)-pyrazol-5-one,
3-methyl-1-(α-methyl-3-methylbenzyl)-pyrazol-5-one,
3-methyl-1-(α-methyl-4-ethylbenzyl)-pyrazol-5-one,
3-methyl-1-(α-methyl-4-chloro-3-methyl)-pyrazol-5-one,
3-methyl-1-(α-methyl-4-fluoro-3-methyl)-pyrazol-5-one,
3-methyl-1-(α-methyl-3-methyl-5-chlorobenzyl)-pyrazol-5-one,
3-methyl-1-(α-methyl-3,5-dimethylbenzyl)-pyrazol-5-one,
3-methyl-1-(α-methyl-3-chloro-4-trifluoromethylbenzyl)-pyrazol-5-one,
3-methyl-1-(α-methyl-3-methyl-4-trifluoromethylbenzyl)-pyrazol-5-one,
3-methyl-1-(α-methyl-3-methoxybenzyl)-pyrazol-5-one,
3-methyl-1-(α-methyl-4-ethoxybenzyl)-pyrazol-5-one,
3-methyl-1-(α-methyl-3-ethylbenzyl)-pyrazol-5-one,
3-methyl-1-(α-methyl-3,4-difluorobenzyl)-pyrazol-5-one*,
3-methyl-1-(α-(3-pyridyl)-ethyl)-pyrazol-5-one*,
3-methyl-1-(α-methyl-3,4-tetramethylenebenzyl)-pyrazol-5-one*,
3-methyl-1-(α-methyl-2,3-tetramethylenebenzyl)-pyrazol-5-one*, 3-ethyl-1-(α-methyl-3-methyl-4-chlorobenzyl)-pyrazol-5-one,
3-ethyl-1-(α-methyl-3-chloro-4-methylbenzyl)-pyrazol-5-one,
3-ethyl-1-(α-methyl-3,4-dichlorobenzoyl)-pyrazol-5-one,
3-ethyl-1-(α-methyl-4-trifluoromethoxybenzyl)-pyrazol-5one,
3-ethyl-1-(α-methyl-4-methyl-3-trifluoromethylbenzyl)-pyrazol-5-one,
3-ethyl-1-(α-methyl-4-bromo-3-chlorobenzyl)-pyrazol-5-one,
3-isopropyl-1-(α-methyl-3,4-dichlorobenzyl)-pyrazol-5-one,
3-trifluoromethyl-1-(α-methyl-4-chlorobenzyl)-pyrazol-5-one*,
3-trifluoromethyl-1-(α-methyl-3-chlorobenzyl)-pyrazol-5-one*,
3-trifluoromethyl-1-(α-methyl-4-bromobenzyl)-pyrazol-5-one*,
3-trifluoromethyl-1-(α-methyl-4-fluorobenzyl)-pyrazol-5-one*,
3-trifluoromethyl-1-(α-methyl-3-chloro-4-methyl)-pyrazol-5-one*,
3-trifluoromethyl-1-(α-(naphthyl-(2))-ethyl)-pyrazol-5-one*,
3-trifluoromethyl-1-(α-methyl-3-bromo-4-chlorobenzyl)-pyrazol-5-one*,
3-phenyl-1-(α-methyl-3,4-dichlorobenzyl)-pyrazol-5-one,
3-phenyl-1-(α-methyl-3-chloro-4-methylbenzyl)-pyrazol-5-one,
3-phenyl-1-(α-methyl-3-methyl-4-chlorobenzyl)-pyrazol-5-one,
3-phenyl-1-(α-n-propylbenzyl)-pyrazol-5-one,
3-phenyl-1-(α-ethyl-3,4-dichlorobenzyl)-pyrazol-5-one,
3-phenyl-4-methyl-1-(α-methylbenzyl)-pyrazol-5-one,
3-phenyl-4-methyl-1-(α-methyl-4-trifluoromethylbenzyl)-pyrazol-5-one,
3-phenyl-4-methyl-1-(α-methyl-3,4-dichlorobenzyl)-pyrazol-5-one,
3-phenyl-4-ethyl-1-(α-methyl-3-chloro-4-methoxybenzyl)-pyrazol-5-one, and
3-phenyl-4-ethyl-1-(α-ethyl-3,4-dimethylbenzyl)-pyrazol-5-one.

The compounds of the present invention are particularly useful for oral or parenteral administration in effecting diuresis and saluresis and can therefore be used for the treatment of oedematous and hypertonic conditions and for flushing out toxic substances.

The compound of Example 6, which is representative of the pyrazol-5-ones of the present invention, was tested in dogs and the following data is representative of the diuretic and saluretic activity of the compounds of the present invention. The activity of two additional compounds are set forth in Table II.

DIURESIS EXPERIMENT WITH DOGS a. Method

Beagle bitches were used. On the day of the experiment, the animals were given 1 ml/kg of a solution which contained 0.4% of NaCl and 0.2% of KCl every 30 minutes by means of a probang. Thereafter, the test preparation was administered orally and the urine was collected. A change in the excretion of electrolyte was detected through comparison with control groups which were given the solvents used. The amounts of urine were converted to ml/kg. It was then possible to calculate the excretion in μequivalent/kg from the volume of urine and the measured electrolyte concentration. Sodium and potassium were determined by flame photometry and chloride was determined potentiometrically.

b. Results

The results are shown in Table I and II. The renal excretion of sodium and water was increased substantially after oral administration of the test preparation. The effect depended on the dose.

Table I

| | | Excretion in ml or μmol/kg/30 minutes Minutes after administration | | | | | | Total excretion after administration |
|---|---|---|---|---|---|---|---|---|
| | | 1–30 | 31–60 | 61–90 | 91–120 | 121–150 | 151–180 | |
| Control | Urine | 1.1 | 1.3 | 1.3 | 1.4 | 1.4 | 0.7 | 7.2 |
| | Na$^+$ | 68 | 79 | 45 | 57 | 51 | 36 | 336 |
| | K$^+$ | 88 | 88 | 64 | 45 | 42 | 25 | 352 |
| 1 mg/kg p.o. | Urine | 4.5 | 11.9 | 4.6 | 3.9 | 1.0 | 0.6 | 26.5 |
| | Na$^+$ | 358 | 1,238 | 535 | 428 | 64 | 14 | 2,637 |
| | K$^+$ | 170 | 259 | 165 | 212 | 102 | 67 | 975 |
| 3 mg/kg p.o. | Urine | 10.0 | 16.1 | 9.8 | 5.0 | 2.5 | 2.0 | 45.4 |
| | Na$^+$ | 969 | 1,932 | 1,251 | 622 | 283 | 218 | 5,275 |
| | K$^+$ | 216 | 259 | 216 | 152 | 119 | 103 | 1,065 |

Effect of 3-methyl-1-(α-methyl-3,4-dichlorobenzyl)-pyrazol-5-one on the renal excretion of electrolyte and excretion of water of conscious dogs, in respect of variation with time and total effect after 3 hours (average values for groups of 4 animals).

Table Ia

| Dose mg/ kg i.v. | | Control Periods of 15 minutes | | Excretion in ml or μmol/kg/15 minutes Administration Periods of 15 minutes | | | | | | Total effect |
|---|---|---|---|---|---|---|---|---|---|---|
| | | 1. | 2. | 3. 1st period after administration | 4. | 5. | 6. | 7. | 8. 6th period after administration | Total excretion after administration (3rd – 8th period) |
| 0.3 | Urine | 2.6 | 3.0 | 5.4 | 7.4 | 6.9 | 6.0 | 5.3 | 4.8 | 35.8 |
| | Na$^+$ | 16 | 13 | 266 | 516 | 502 | 469 | 418 | 361 | 2,532 |
| | K$^+$ | 12 | 12 | 53 | 74 | 52 | 43 | 38 | 27 | 287 |

Table Ia-continued

| Dose mg/kg i.v. | | Control Periods of 15 minutes | | Administration Periods of 15 minutes | | | | | Total effect |
|---|---|---|---|---|---|---|---|---|---|
| | | \multicolumn{2}{c}{} | \multicolumn{5}{c}{Excretion in ml or μmol/kg/15 minutes} | | |
| 1.0 | Urine | 2.7 | 3.7 | 9.5 | 14.8 | 14.3 | 13.9 | 12.9 | 11.7 | 77.1 |
| | Na+ | 16 | 20 | 885 | 1,565 | 1,467 | 1,363 | 1,272 | 1,181 | 7,733 |
| | K+ | 31 | 24 | 103 | 127 | 113 | 109 | 107 | 98 | 657 |

Effect of 3-amino-1-(α-methyl-3,4-dichlorobenzyl)-pyrazol-5-one on the renal excretion of electrolyte and excretion of water of conscious dogs, in respect of variation with time and total effect after 1.5 hours (average values for groups of 4 animals).

| | Excretion in μ equivalent or ml/kg/1 hour | | | |
|---|---|---|---|---|
| | | Na+ | K+ | H$_2$O |
| Control | | 168 | 136 | 2.4 |
| (4-methylphenyl compound) | 3 mg/kg p.o. | 1158 | 358 | 10.5 |
| (4-bromophenyl compound) | 3 mg/kg p.o. | 1106 | 334 | 8.7 |

The pharmaceutical compositions of the present invention contain a major or minor amount, e.g., 0.1% to 99.5%, preferably 0.5% to 90%, of active ingredient as above defined in combination with a pharmaceutically acceptable, nontoxic, inert diluent or carrier, the carrier comprising one or more solid, semi-solid or liquid diluent, filler and formulation adjuvant which is nontoxic, inert and pharmaceutically acceptable. Such pharmaceutical compositions are preferably in dosage unit form; i.e., physicall discrete units containing a predetermined amount of the drug corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day. Other therapeutic agents can also be present.

Although the dosage and dosage regimen must in each case be carefully adjusted, utilizing sound professional judgment and considering the age, weight and condition of the recipient, the route of administration and the nature and gravity of the illness, generally the dosage for parenteral administration will be from 0.1 to 50, and preferably 0.1 to 10 mg/kg of body weight per day, whereas the oral dosage will be 0.1 to 500, and preferably 0.5 to 100 mg/kg of body weight per day. In some instances a sufficient therapeutic effect can be obtained at a lower dose, while in others, a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate as for example starch, lactose, sucrose, glucose or mannitol. Sweetening, flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated for example by preparing a powder mixture, granulating or slugging, adding a lubricant and disintegrant and pressing into tablets. A powder mixture is prepared by mixing the compound, suitable comminuted, with a diluent or base as described above, and optionally with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The power mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet-forming dies by means of the addition of stearic acid, a stearate salt, talc or mineral oil. The lubricated mixture is then compressed into tablets. The medicaments can also be combined with free-flowing, inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous sucrose solution while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a non-toxic liquid vehicle suitable for injection such as an aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example myristyl palmitate, or mixtures thereof.

The preferred daily dose for parenteral administration is 0.5 mg to 5 g, particular 5 mg to 1 g, of active agent; for oral administration the preferred daily dosage of active agent is 5 mg to 50 g, particularly 25 mg to 10 g.

While the routes of administration include oral parenteral (i.e., intramuscular, intraperitoneal, and intravenous), and rectal, oral administration and parenteral administration are particularly preferred.

The preferred pharmaceutical compositions are therefore those in a form suitable for oral administration such as tablets and suspensions and those suitable for parenteral administration such as solutions and suspensions.

Examples A and B set forth below are illustrative of pharmaceutical compositions embodying the compounds of the present invention:

EXAMPLE A 200 g of 3-amino-1-(α-methyl-4-chlorobenzyl)-pyrazol-5-one are ground to a powder and mixed with 300 g of lactose and 200 g of potato starch, and after moistening with an aqueous gelatine solution the mixture is granulated through a sieve.

After drying, 60 g of talc and 5 g of sodium laurylsulphate are added. About 10,000 tablets each containing 20 mg of active compound are pressed from this mixture.

EXAMPLE B 20 g of the sodium salt of 3-methyl-1-(α-methyl-3-chlorobenzyl)-pyrazol-5-one are dissolved in 1,000 ml of propylene glycol and the solution is made up to 5,000 ml with water. This solution is filled under aseptic conditions into sterile ampoules each of 5 ml capacity and each containing 20 mg of active compound.

The following nonlimitative examples more particularly illustrate the present invention:

EXAMPLE 1

(3-methyl-1-(α,4-dimethylbenzyl)-pyrazol-5-one)

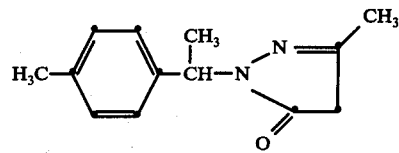

26 g of acetoacetic acid ethyl ester were dissolved in 20 ml of absolute ethanol. 30.0 g of α-methyl-4-methylbenzylhydrazine in a little absolute ethanol were slowly added to this solution under nitrogen. After the exothermic reaction had subsided, the mixture was heated for 2 hours under reflux. On cooling, the crude product crystallized out and was purified by recrystallization from methanol. Melting point 144°–146° C; yield 28 g (65% of theory).

The following compounds were produced in a manner analogous to that described in Example 1 from the reactants set forth:

| No. | Structural formula | Recrystallization from | Yield | Melting point ° C |
|-----|-------------------|------------------------|-------|-------------------|
| 2   |                   | Dimethylformamide      | 63    | 150 – 152         |
| 3   |                   | Ethanol                | 77.7  | 143 – 145         |

-continued

| No. | Structural formula | Recrystallization from | Yield | Melting point °C |
|---|---|---|---|---|
| 4 | 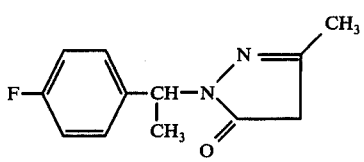 | Methanol | 80 | 140 – 142 |

EXAMPLE 5

(3-Methyl-1-(α-methyl-4-fluorobenzyl)-pyrazol-5-one)

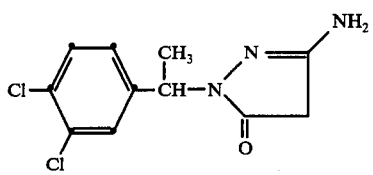

8.3 g (0.074 mol) of tetrolic acid ethyl ester and 11.3 g of α-methyl-4-fluorobenzylhydrazine in 70 ml of n-butanol were heated for 8 hours under reflux.

The solution was concentrated and the solid residue was recrystallized from ethanol.

Melting point 140°–142° C; yield 4 g (25% of theory).

EXAMPLE 6

(3-Amino-1-(α-methyl-3,4-dichlorobenzyl)-pyrazol-5-one)

41 g of α-methyl-3,4-dichlorobenzylhydrazine, dissolved in absolute ethanol, were added dropwise to a solution of 31.8 g of β-amino-β-ethoxyacrylic acid ethyl ester and 1.5 g of p-toluenesulphonic acid in 150 ml of ethanol at room temperature under nitrogen gas. After stirring for 2 hours and standing overnight, the reaction solution was concentrated as far as possible on a rotary evaporator. The residue which remained was dissolved in 2 N sodium hydroxide solution. Any unconverted starting products or by-products were extracted with ether. The aqueous phase was then brought to pH 5 with acetic acid. The oil thereby produced was taken up in methylene chloride and the organic phase was dried over $Na_2SO_4$. After evaporating off the solvent, the reaction product crystallized out. It was recrystallized from methanol. Melting point 127°–129° C; yield 21 g (38.5% of theory).

EXAMPLE 7

(3,4-dimethyl-1-(α,4-dimethylbenzyl)-pyrazol-5-one)

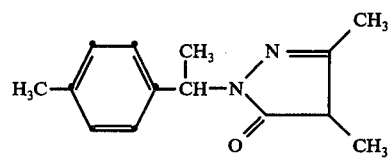

30 g of α-methyl-4-methylbenzylhydrazine in ethanol were added to a solution of 28.8 g (0.2 mol) of α-methyl-acetoacetic acid ethyl ester in 40 ml of ethanol under $N_2$ gas; during the addition, the temperature rose to 70° C. After completion of the addition, the reaction mixture was heated for 2 hours under reflux.

On cooling, the reaction product crystallized out. It was recrystallized from methanol.

Melting point 131°–133° C; yield 27 g (59% of theory).

The following compounds were produced in a manner analogous to that described in Example 7 from the reactants set forth:

| No. | Structural formula | Recrystallization from | Yield, % of theory | Melting point °C |
|---|---|---|---|---|
| 8 | | Ethanol | 60 | 160–162 |
| 9 | | Methanol | 65 | 145–147 |

| No. | Structural formula | Recrystallization from | Yield, % of theory | Melting point °C |
|---|---|---|---|---|
| 10 | 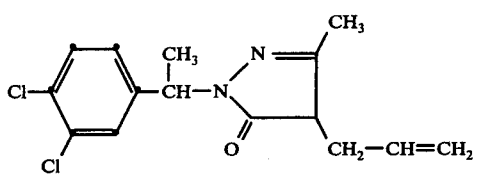 | Ethanol | 43 | 102–104 |

EXAMPLE 11

(3-Methyl-4-(prop-2-en-1-yl)-1-(α-methyl-3,4-dichlorobenzyl)-pyrazol-5-one).

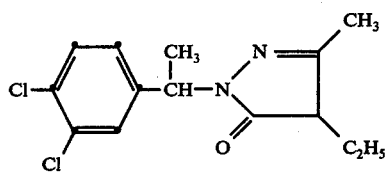

17 g (0.1 mol) of allylacetoacetic acid ethyl ester were added to a mixture of 20.5 g of α-methyl-3,4-dichorobenzylhydrazine and 30 ml of absolute ethanol under nitrogen, whereupon the temperature rose to 55° C. The reaction mixture was heated to the reflux temperature for 2 hours. After cooling, the reaction product crystallized out Melting point 124° to 125° C; yield 23.0 g (75% of theory).

The following compound was produced in a manner analogous to that described in Example 11 from the reactants set forth:

| No. | Structural formula | Recrystallization from | Yield, % of theory | Melting Point °C |
|---|---|---|---|---|
| 12 | H₃C—⌬—CH(CH₃)—N—N=... CH₂—CH=CH₂ | Ethanol | 48.5 | 138–139 |

EXAMPLE 13

(3-Methyl-4-ethyl-1-(α-methyl-3,4-dichlorobenzyl)-pyrazol-5-one).

25.2 g of 3-methyl-4-ethylpyrazol-5-one were added in portions to a suspension of 10.0 g (0.22 mol) of sodium hydride in 200 ml of absolute dimethylformamide. After the evolution of H₂ had ceased, 41.8 g (0.2 mol) of α-methyl-3,4-dichlorobenzyl chloride were added dropwise to the reaction solution. The mixture was then stirred for 2 hours at 60° C, the solvent was distilled off in vacuo and the residue was taken up in water and acidified with dilute acetic acid. The crude product thereby obtained was recrystallized from ethanol.

Melting point 153°–155° C; yield 16.7 g (28% of therory).

EXAMPLE 14

(3-Methyl-4-phenyl-1-(α-methyl-3,4-dichlorobenzyl)-pyrazol-5-one).

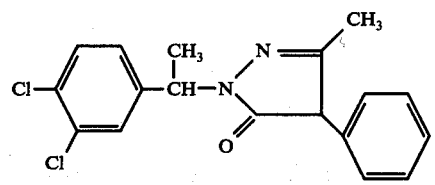

20.6 g of α-phenylacetoacetic acid ethyl ester were added dropwise under nitrogen to a solution of 20.5 g (0.1 mol) of α-methyl-3,4-dichlorobenzylhydrazine in 20 ml of absolute ethanol, during which the temperature of the reaction mixture rose to 55° C. After heating the reaction solution for 2 hours under reflux, the reaction product crystallized out on cooling the reaction mixture. The crystals were filtered off, rinsed with ether and recrystallized from an ethanol/dimethyl formamide mixture.

Melting point 214°–216° C; yield 26 g (75% of theory).

EXAMPLE 15

(3-Methyl-4-(4-methoxybenzyl)-1-(α,4-dimethylbenzyl)-pyrazol-5-one).

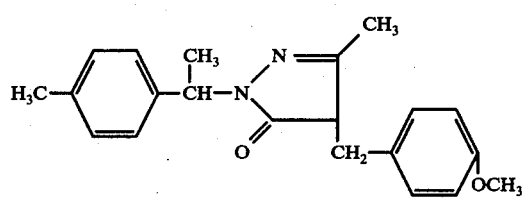

31 g of α-(4-methoxybenzyl)-acetoacetic acid ethyl ester were added to a solution of 15 g of α-methyl-4-methylbenzylhydrazine in 30 ml of absolute ethanol in an inert gas atmosphere, during which the temperature of the reaction mixture rose to 60° C. After heating for 2 hours under reflux and standing overnight, the product crystallized out and was recrystallized from a mixture of ethanol and a little dimethylformamide.

Melting point 146°–147° C; yield 20 g (60% of theory).

The following compounds were produced in a manner analogous to that described in Example 15 from the reactants set forth;

| No. | Structural formula | Recrystallization from | Yield, % of theory | Melting Point ° C |
|---|---|---|---|---|
| 16 | 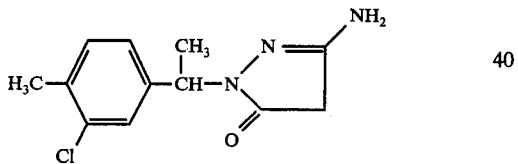 | Ethanol | 64 | 172–174 |
| 17 | 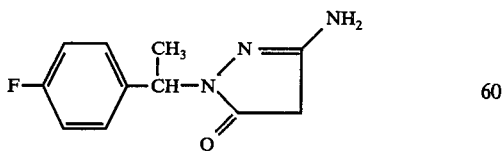 | Dimethylformamide/ ethanol | 73 | 175–177 |

EXAMPLE 18

(3-Amino-1-(α,4-dimethyl-3-chlorobenzyl)-pyrazol-5-one).

0.2 mol of 1-(α-methyl-3-chloro-4-methylbenzyl)-3-chloropyrazol-5-one was dissolved in 100 ml of ethanol, 17 g of ammonia were added and the mixture was heated to 150° C for 2 hours in a stirred autoclave. After concentrating the reaction solution, the crude product was obtained. It was recrystallized twice from ethanol.

Melting point 86°–88° C; yield 4.2 g (8.5% of theory).

EXAMPLE 19

(3-Amino-1-(α-methyl-4-fluorobenzyl)-pyrazol-5-one)

0.1 mol of (1-(α-methyl-4-fluorobenzyl)-3-ethoxycarbonylamino-pyrazol-5-one was boiled in 200 ml of aqueous Zn hydrochloric acid for 2 hours under reflux after addition of 40 ml of glacial acetic acid. After cooling, and neutralization with dilute sodium hydroxide solution, crystalline product could be filtered off. The product was recrystallized from a little ethanol.

Melting point 128°–130° C; yield 17.5 g (79% of theory).

EXAMPLE 20

(3-Methyl-1-(2-[α-pyrid-4-yl]-ethyl)-pyrazol-5-one)

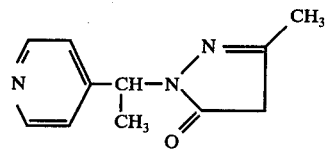

This compound is obtained from acetoacetic acid ethyl ester and α-pyridyl-(4)-ethylhydrazine. It is recrystallized from ethanol.

Melting point 146°–148° C; yield 42% of theory.

EXAMPLE 21

(3-Methyl-1-(α-[β-naphthyl]-ethyl)-pyrazol-5-one)

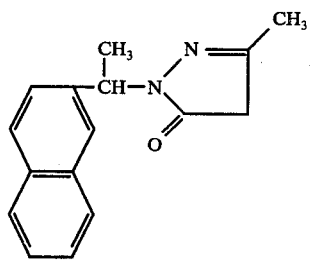

This compound was obtained from α-naphthyl-(2)-ethylhydrazine and acetoacetic acid ethyl ester. It was recrystallized from ethanol.

Melting point 145°–147° C; yield 35% of theory.

EXAMPLE 22

(3-Trifluoromethyl-1-(α-methyl-3,4-dichlorobenzyl)-pyrazol-5-one)

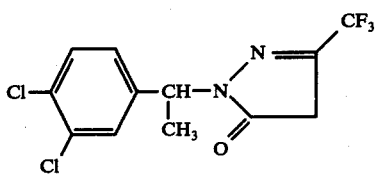

This compound was obtained from trifluoroacetoacetic acid ethyl ester and α-methyl-3,4-dichlorobenzylhydrazine. It was recrystallized from ether/ethanol.
Melting point 203°–205° C; yield 23% of theory.

EXAMPLE 23

(3-Trifluoromethyl-1-(α-methyl-4-fluorobenzyl)-pyrazol-5-one)

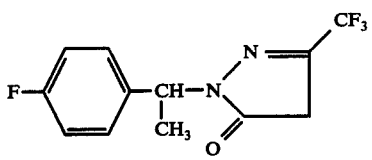

This compound was obtained from trifluoroacetoacetic acid ethyl ester and α-methyl-4-fluorobenzylhydrazine. It was purified by precipitation from ether with petroleum ether.
Melting point 168°–170° C; yield 32% of theory.

EXAMPLE 24

(3-Phenyl-1-(α-ethylbenzyl)-pyrazol-5-one)

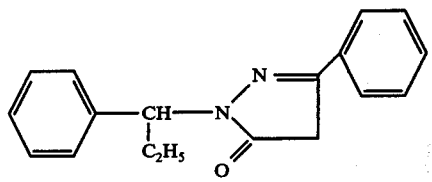

This compound was obtained from benzoylacetic acid ethyl ester and α-methylbenzylhydrazine. It was recrystallized from dimethylformamide.
Melting point 170°–172° C; yield 78% of theory.

EXAMPLE 25

(3-Phenyl-1-(α-methyl-3,4-dichlorobenzyl)-pyrazol-5-one)

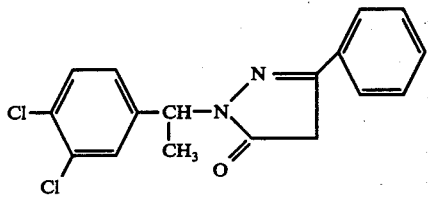

This compound was obtained from benzoylacetic acid ethyl ester and α-methyl-3,4-dichlorobenzylhydrazine. It was recrystallized from dimethylformamide.
Melting point 155°–157° C; yield 86% of theory.

What is claimed:
1. A compound of the formula

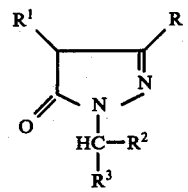

or a pharmaceutically acceptable, nontoxic salt thereof, wherein
$R$ is hydrogen, lower alkyl, lower alkenyl, phenyl or trifluoromethyl;
$R^1$ is monoaryl unsubstituted or substituted by lower alkoxy or aralkyl wherein the aryl moiety is a monoaryl moiety and the alkyl moiety is a lower alkyl moiety, said aralkyl being unsubstituted or substituted by lower alkoxy;
$R^2$ is lower alkyl; and
$R^3$ is aryl of 6 to 10 carbon atoms substituted by:
   a. 1 or 2 of the same or different substituents selected from the group consisting of halogen, trifluoromethyl, lower alkyl, lower alkenyl and lower alkoxy;
   b. cycloalkyl of 5, 6 or 7 carbon atoms or cycloalkenyl of 5, 6 or 7 carbon atoms;
   c. nitro; or
   d. a substituent selected from the group consisting of trifluoromethyl and nitro, and 1 or 2 of the same or different substituents selected from the group consisting of lower alkyl, lower alkenyl, lower alkoxy, halogen and trifluoromethyl; or
$R^3$ is naphthyl.
2. A compound according to claim 1 wherein
$R^3$ is aryl of 6 to 10 carbon atoms substituted by:
   a 1 or 2 of the same or different substituents selected from the group consisting of halogen, trifluoromethyl, lower alkyl, lower alkenyl and lower alkoxy;
   b. nitro; or
   c. a substituent selected from the group consisting of trifluoromethyl and nitro, and 1 or 2 of the same or different substituents selected from the group consisting of lower alkyl, lower alkenyl, lower alkoxy, halogen and trifluoromethyl; or
$R^3$ is naphthyl.
3. A compound according to claim 1 wherein
$R$ is hydrogen, alkyl of 1 to 4 carbon atoms, alkenyl of 2 to 4 carbon atoms, phenyl, or trifluoromethyl;
$R^1$ is phenyl unsubstituted or substituted by alkoxy of 1 to 4 carbon atoms or benzyl unsubstituted or substituted by alkoxy of 1 to 4 carbon atoms;
$R^2$ is alkyl of 1 to 4 carbon atoms;
$R^3$ is naphthyl; or phenyl substituted by:
   a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
   nitro; or
   c. a substituent selected from the group consisting of trifluoromethyl and nitro, and 1 or 2 of the same or different substituents selected from the group consisting of alkyl of 1 to 4 carbon atoms, alkenyl of 2 to 4 carbon atoms, alkoxy of 1 to 4 carbon atoms, halogen and trifluoromethyl.

4. A compound according to claim 1 wherein
R is hydrogen, alkyl of 1 to 4 carbon atoms, alkenyl of 2 to 4 carbon atoms, or phenyl;
R¹ is phenyl unsubstituted or substituted by alkoxy of 1 to 4 carbon atoms or benzyl unsubstituted or substituted by alkoxy of 1 to 4 carbon atoms;
R² is alkyl of 1 to 4 carbon atoms;
R³ is naphthyl; or phenyl substituted by:
  a. 1 or 2 of the same or different substituents selected from the group consisting of halogen, trifluoromethyl, alkyl of 1 to 4 carbon atoms, alkenyl of 2 to 4 carbon atoms and alkoxy of 1 to 4 carbon atoms;
  b. nitro; or
  c. trifluoromethyl and nitro, and 1 or 2 of the same or different substituents selected from the group consisting of alkyl of 1 to 4 carbon atoms, alkenyl of 2 to 4 carbon atoms; alkoxy of 1 to 4 carbon atoms, halogen and trifluoromethyl.

5. A compound according to claim 1 wherein
R is hydrogen, alkyl of 1 to 4 carbon atoms, phenyl or trifluoromethyl;
R¹ is phenyl, benzyl or phenyl or benzyl substituted by alkoxy of 1 or 2 carbon atoms;
R² is alkyl of 1 to 4 carbon atoms;
R³ is naphthyl; or phenyl substituted by:
  a. 1 or 2 straight or branched-chain alkyl moieties of 1 to 8 carbon atoms, or alkenyl moieties of 2 to 8 carbon atoms;
  b. 1 or 2 alkoxy moieties of 1 to 6 carbon atoms;
  c. cycloalkyl of 5, 6 or 7 carbon atoms or cycloalkenyl of 5, 6 or 7 carbon atoms;
  d. 1 or 2 halogens;
  e. 1 or 2 trifluoromethyl moieties; or
  f. nitro.

6. A compound according to claim 1 wherein
R is hydrogen, methyl, ethyl, phenyl or trifluoromethyl;
R¹ is phenyl, benzyl, or phenyl or benzyl substituted by alkoxy of 1 or 2 carbon atoms;
R² is alkyl of 1 to 4 carbon atoms;
R³ is naphthyl; or phenyl substituted by:
  a. 1 or 2 straight or branched-chain alkyl moieties of 1 to 4 carbon atoms;
  b. 1 or 2 alkoxy moieties of 1 to 4 carbon atoms;
  c. cycloalkyl of 5, 6 or 7 carbon atoms or cycloalkenyl of 5, 6 or 7 carbon atoms;
  d. 1 or 2 fluoro, chloro or bromo moieties;
  e. 1 or 2 trifluoromethyl moieties; or
  f. nitro.

7. A compound according to claim 1 wherein
R is hydrogen, methyl, ethyl or phenyl; R¹ is phenyl, benzyl, or phenyl or benzyl substituted by alkoxy of 1 or 2 carbon atoms;
R² is alkyl of 1 to 4 carbon atoms;
R³ is naphthyl; or phenyl substituted by:
  a. 1 or 2 straight or branched-chain alkyl moieties of 1 to 4 carbon atoms;
  b. 1 or 2 alkoxy moieties of 1 to 4 carbon atoms;
  c. cycloalkyl of 5, 6 or 7 carbon atoms or cycloalkenyl of 5, 6 or 7 carbon atoms;
  d. 1 or 2 fluoro, chloro or bromo moieties;
  e. 1 or 2 trifluoromethyl moieties; or
  f. nitro.

8. A compound according to claim 1 wherein
R is alkyl of 1 or 2 carbon atoms, phenyl or trifluoromethyl;
R¹ is phenyl, benzyl or methoxybenzyl;
R² is alkyl of 1 or 2 carbon atoms; and
R³ is naphthyl; or phenyl substituted by chlorine, fluorine, bromine, methyl, dichlorine or chlorine and methyl.

9. A compound according to claim 1 wherein
R is methyl, phenyl or trifluoromethyl;
R¹ is phenyl, benzyl or methoxybenzyl;
R² is methyl; and
R³ is naphthyl; or phenyl substituted by fluorine, bromine, methyl, dichlorine or chlorine and methyl.

10. A compound according to claim 1 wherein
R is methyl or phenyl;
R¹ is phenyl, benzyl or methoxybenzyl;
R² is methyl; and
R³ is naphthyl; or phenyl substituted by fluorine, bromine, methyl, dichlorine or chlorine and methyl.

11. A compound according to claim 1 wherein R is hydrogen, lower alkyl or lower alkenyl.

12. The compound according to claim 1 which is

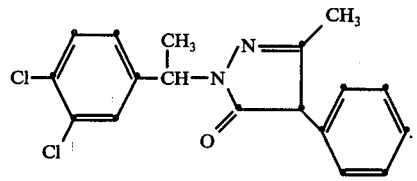

13. The compound according to claim 1 which is

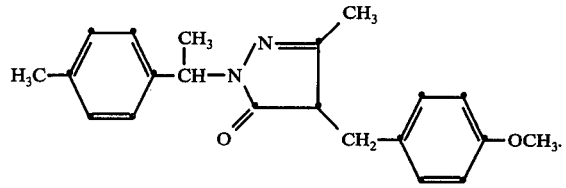

14. The compound according to claim 1 which is

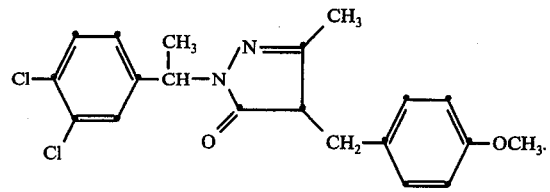

15. The compound according to claim 1 which is

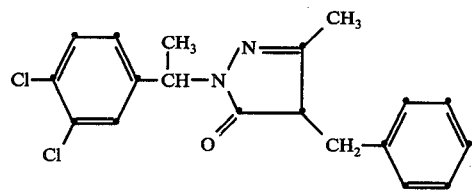

* * * * *